United States Patent [19]

McCombie et al.

[11] Patent Number: 4,762,827

[45] Date of Patent: Aug. 9, 1988

[54] (5R,6S,8R)-6-(1-HYDROXYETHYL)-2-(3R-PYRROLIDIN-2-ONE-3-YL)THIOPENEM-3-CARBOXYLIC ACID

[75] Inventors: Stuart W. McCombie, Caldwell; Jayaram R. Tagat, Westfield, both of N.J.

[73] Assignee: Schering Corporation, Kenilworth, N.J.

[21] Appl. No.: 59,720

[22] Filed: Jun. 9, 1987

Related U.S. Application Data

[63] Continuation-in-part of Ser. No. 900,066, Aug. 25, 1986, abandoned.

[51] Int. Cl.$^4$ .................. C07D 499/00; A61K 31/425

[52] U.S. Cl. .................. 514/192; 514/195; 540/310

[58] Field of Search ................. 540/310; 514/192, 195

[56] References Cited

U.S. PATENT DOCUMENTS 4,530,793  7/1985  Girijavallabhan et al. ......... 540/310

*Primary Examiner*—Nicholas S. Rizzo
*Attorney, Agent, or Firm*—Richard C. Billups; James R. Nelson; Stephen I. Miller

[57] ABSTRACT

There is disclosed the compound (5R,6S,8R)-6-(1-hydroxyethyl)-2-(3R-pyrrolidin-2-one-3-yl)thiopenem-3-carboxylic acid, and pharmaceutically acceptable salts and esters as well as compositions containing them and methods for their use.

14 Claims, No Drawings

(5R,6S,8R)-6-(1-HYDROXYETHYL)-2-(3R-PYRROLIDIN-2-ONE-3-YL)THIOPENEM-3-CARBOXYLIC ACID

CROSS-REFERENCE TO RELATED APPLICATIONS

This application is a continuation-in-part of U.S. application Ser. No. 900,066, filed on Aug. 25, 1986, co-pending herewith, now abandoned.

BACKGROUND OF THE INVENTION

This invention relates to (5R,6S,8R)-6-(1-hydroxyethyl)-2-(3R-pyrrolidin-2-one-3-yl)thiopenem-3-carboxylic acid and pharmaceutically acceptable salts and esters thereof, which compounds possess potent antibacterial activity.

U.S. Pat. No. 4,530,793, and Japanese Disclosure No. 57-176988 each generically disclose a thiopyrrolidone substituent attached to a penem ring. However, the specific stereoisomers of this invention are not disclosed or contemplated. The compounds of this invention exhibit superior antibacterial activity compared to the prior art compounds.

There currently exists a need for new antibacterial agents since continued extensive use of antibacterials gives rise to resistant strains of pathogens, rendering them less effective. Additionally, in certain clinical instances, the antibacterial compounds currently used manifest clinical toxicity limiting the use of such compounds. Consequently, this invention addresses these and other present needs.

SUMMARY OF THE INVENTION (5R,6S,8R)-6-(1-hydroxyethyl)-2-(3R-pyrrolidin-2-one-3-yl)thiopenem-3-carboxylic acid, pharmaceutically acceptable salts and pharmaceutically acceptable esters thereof possess antibacterial activity against both gram-positive and gram-negative bacteria. In particular, the 3R-pyrrolidin-2-one shows unexpectedly potent antibacterial activity over the 3S-form and over the racemic mixture, such that the 3R-form is useful in oral, parenteral and topical preparations as an antibacterial agent.

The invention also involves a pharmaceutical composition which comprises a compound above described, in combination with a pharmaceutical carrier.

The invention further involves a method of treating susceptible infections comprising administering the above defined pharmaceutical composition to a mammal in an amount effective to treat such infection.

The compounds described herein are advantageous in that they demonstrate antibacterial activity at lower concentrations than compounds currently in use.

DETAILED DESCRIPTION

When tested in standardized microbiological assays, the compounds of this invention are active against such gram-positive organisms as *Staphlococcus aureus* and *Bacillus subtilis,* and such gram-negative organisms as *E. coli* and Salmonella, at test levels of 0.016 to 5.66 mcg/ml. Additionally, the subject compounds show activity against organisms which produce beta-lactamases, e.g., penicillinase and cephalosporinase, indicating a resistance to degradation by these enzymes. For instance, the sodium salt of (5R,6S,8R)-6-(1-hydroxyethyl)-2-(3R-pyrrolidin-2-one-3-yl)thiopenem-3-carboxylic acid is active against *Staphlococcus aureus* at a test level of 0.125 mcg/ml. When tested against *E. coli* 71120101 (a beta-lactamase producing organism) the compound exhibits activity at 0.1250 microgram/ml.

The compounds of this invention exhibit low protein binding and their metabolites have little or no unpleasant odor.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, the compounds may be formulated into solutions or suspensions. Typical topical formulations are those such as lotions, creams, ointments, sprays, and mechanical delivery devices, e.g., transdermal.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants; ethylene gylcol polymers; beta-cyclodextrin; fatty alcohols; hydrolyzed cereal solids; water; polyalkylene gylcols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, i.e., the age and weight of the individual being treated, the mode of administration, and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

As used herein, "pharmaceutically acceptable salts" means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cycloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. For example, salts of the compound can be formed by treating it with metal compounds such as alkali metal salts of suitable carboxylic acids, or with ammonia or a suitable organic amine, wherein preferably stoichiometric amounts or only a small-excess of the salt-forming agent is used. The pharmaceutically acceptable esters are preparable in a manner analogous to the preparation of the corresponding esters of penicillins and cephalosporins.

The following process may be employed to produce (5R,6S,8R)-6-(1-hydroxyethyl)-2-(3R-pyrrolidin-2-one-3-yl)thiopenem carboxylic acid, and related salts and esters thereof.

The compound (S)-3-hydroxy pyrrolidin-2-one may be produced from methyl (S)-4-benzyloxycarbonylamino-2-hydroxybutyrate by reaction in an acidified inert organic solvent by catalytic reduction, followed by neutralization.

For example, a small quantity of concentrated hydrochloric acid is used to acidify a methanol reaction medium, and palladium/carbon is introduced under nitrogen to act as a reduction catalyst. After reduction with hydrogen, a base such as triethylamine is introduced, and the mixture is heated in an inert solvent such as benzene. The (S)-3-hydroxy pyrrolidin-2-one product is then reacted at about 0° C. in an anhydrous inert solvent, e.g. an alkylene dihalide, such as methylene chloride with methane sulfonyl chloride and triethylamine to yield an (S)-lactam-O-mesylate e.g. (S)-3-methane sulfonyloxypyrrolidin-2-one. Alternatively, the (S)-lactam-O-mesylate can be produced in adequate yield from the crude hydroxylactam hydroxypyrrolidin-2-one without isolating (S)-3-hydroxypyrrolidin-2-one.

The lactam mesylate is then subsequently reacted with a metal salt preferably potassium, of an esterified thiopenem which may be produced in accordance with the disclosure of U.S. Pat. No. 4,559,333 to produce the corresponding esterified penem. For example, allyl (5R,6S,8R)-6-(1-hydroxyethyl)-2-potassiumthiopenem-3-carboxylate is reacted with (S)-3-methanesulfonyloxy-pyrrolidin-2-one to form allyl (5R,6S,8R)-6-(1-hydroxyethyl)-2-(3R-pyrrolidin-2-one-3-yl)thiopenem-3-carboxylate.

The allyl group is thereafter easily removed from the carboxyl moiety to form the free carboxylic acid or the sodium carboxylate through reaction with sodium 2-ethylhexanoate or the free acid and a catalyst as disclosed in U.S. Pat. No. 4,314,942. If the free carboxylic acid compound is desired it may be produced through reaction with 2-ethylhexanoic acid to yield (5R,6S,8R)-6-(1-hydroxyethyl)-2-(3R-pyrrolidin-2-one-3-yl)-thiopenem-3-carboxylic acid.

Salts may be alternatively converted in the usual manner into the free carboxy compounds.

The following examples illustrate the preparation of the compounds and compositions of this invention. Unless otherwise specified all temperatures are in degrees Celsius.

EXAMPLE 1

(S)-3-Hydroxy-Pyrrolidin-2-One

Stir at room temperature a solution of (S)-4-benzyloxycarbonylamino-2-hydroxy butyric acid (25.3 g, 100 mmol.) and concentrated HCl (2.0 ml.) in methanol (150 ml.) for 24 hours. Transfer to a Parr bottle and add palladium on carbon (10%, 2.5 g.) under a nitrogen atmosphere. Place the contents under a pressurized hydrogen atmosphere (50 psi) and shake (6 hrs.). Remove the palladium on carbon by filtering through celite. Concentrate the filtrate in vacuo to yield a waxy residue, and dissolve in benzene to form a basic solution. Treat the solution with dry triethylamine (3 ml.), raise to reflux temperature, and stir (4 hrs.). Remove the benzene with a rotary evaporator, and subject the residue to flash chromatography on silica gel (25–50% acetone in dichloromethane) to yield the title compound as a white solid.

200 MHz NMR (CDCl$_3$): $\delta$2.05(m,1H), 2.50(m,1H), 3.35(m,2H), 4.30(t,J=8 Hz,1H), 4.65(br—S,1H—OH) and 7.15(br—S,1H—NH).

M.P.: 75°–77° C.

EXAMPLE 2

(S)-3-Methanesulfonyloxy-Pyrrolidin-2-One

Suspend the product of Example 1 (8 g., 79.2 mmol.) in dry methylene chloride (30 ml.) and cool to 0° C. Treat the suspension sequentially with dry triethylamine (16 ml., 118.8 mmol.) and methane sulfonyl chloride (6.74 ml., 87.12 mmol.). Stir at 5°–10° C. for 1.5 hours, and subject the mixture to flash chromatography using acetone (5–10%) in dichloromethane to yield the title compound as a white solid.

Optical rotation: $[\alpha]_D^{26}$= −68.3° (C=0.62, CHCl$_3$) M.P.: 122°–124° C. 200 MHz NMR(CDCl$_3$): $\delta$2.45(m,2H), 3.20(s,3H), 3.35(m,2H), 5.10(t,J=8 Hz,1H) and 7.75(br-S,1H-NH). MS: 180(M+1).

EXAMPLE 3

Allyl (5R,6S,8R)-6-(1-Hydroxyethyl)-2-(3R-Pyrrolidin-2-One-3-yl)Thiopenem-3-Carboxylate Dissolve the compound of Example 2 (12 g., 67 mmol.) in dimethyl formamide (50 ml.) and treat with allyl (5R,6S,8R)-6-(1-hydroxyethyl)-2-potassiumthiopenem-3-carboxylate. Stir the solution at room temperature for 12 hours. Dilute the reaction mixture with dichloromethane (300 ml.) and wash sequentially with aqueous copper sulfate (5%, 50 ml.), water (50 ml., twice), brine, and dry.

Back extract the combined aqueous layers with chloroform (200 ml.) containing ethyl acetate (10%). Combine all organic layers and concentrate in vacuo to a solid. Recrystallize this solid with methylene chloride or by flash chromatography to yield the title compound as a yellow solid.

200 MHz NMR (DMSO-d$_6$): δ1.2(d,3H); 2.1(m,1H); 2.7(m,1H); 3.3(t,J=5 Hz,2H); 3.85 (d,J=4 Hz,1H); 4.1(m,2H); 4.7(dd,2H); 5.2(d,J=4 Hz,2H); 5.45(d, J=12 Hz,1H); 5.75(s,1 Hz); 5.95(m,1H); 8.1(br—S; 1H—NH).

EXAMPLE 4

Sodium (5R,6S,8R)-6-(1-Hydroxyethyl)-2-(3R-Pyrrolidin-2-One-3-yl)Thiopenem-3-Carboxylate The compound of Example 3 (10 g., 27.2 mmol.) is suspended in methylene chloride (1 l.) containing acetone (10%) and stirred vigorously (1 hr.). Add to the solution sequentially tri isopropyl phosphite (3.35 ml., 13.6 mmol.), sodium 2-ethylhexanoate (4.5 g., 27.2 mmol.) and a catalytic amount of palladium acetate (0.61 g., 2.72 mmol.). Stir (2 hrs.) and remove the solvent with a rotary evaporator to obtain a residue. Dissolve the residue in water (400 ml.) and wash with ethyl acetate (100 ml., 3 times). Pass the aqueous extract through a silica gel pad (3 inch, reverse phase), and wash with water (50 ml.) Combine the aqueous filtrates and lyophilize to yield the title compound as a yellow solid.

200 MHz NMR(D$_2$O): δ1.2(d,3H); 2.1(m,1H); 2.70(m,1H); 3.3(t, J=5 Hz,2H); 3.85(d,J=4 Hz,1H); 4.15(m,2H) and 5.60(s,1H).

In the following examples, the term "Active ingredient" is used to designate the compound (5R, 6S, 8R)-6-(1-hydroxyethyl)-2-(3R-pyrrolidin-2-one-3-yl)thiopenem-3-carboxylic acid and an equivalent amount of pharmaceutically acceptable salts or esters thereof.

EXAMPLE 5

Capsules

| No. | Ingredient | mg/capsule | mg/capsule |
|---|---|---|---|
| 1. | Active ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |
| 5. | Magnesium Stearate NF | 5 | 6.5 |
|  | Total | 500 | 650 |

Method of Manufacture

Mix Items Nos. 1, 2, 3 and 4 in a suitable mixer for 10–15 minutes. Add Item No. 5 and mix for 1–3 minutes. Fill the mixture into suitable two-piece hard gelatin capsules using encapsulating machine.

EXAMPLE 6

Tablets

| No. | Ingredient | mg/capsule | mg/capsule |
|---|---|---|---|
| 1. | Active ingredient | 250 | 500 |
| 2. | Lactose USP | 57 | 114 |
| 3. | Corn Starch, Food Grade, as a 10% paste in Purified Water | 20 | 40 |
| 4. | Corn Starch, Food Grade | 18 | 39 |
| 5. | Magnesium Stearate NF | 5 | 7 |
|  | Total | 350 | 700 |

Method of Manufacture

Mix Items Nos. 1 and 2 in a suitable mixer for 10–15 minutes. Granulate the mixture with Item No. 3. Paste wet granulation through a coarse screen (e.g., ¼") if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

EXAMPLE 7

Injectable Powder: (per vial)

|  | g/vial | g/vial |
|---|---|---|
| Active Ingredient | 0.5 | 1.0 |

Add sterile water for injection or bacteriostatic water for injection for reconstitution.

EXAMPLE 8

Injectable Solution

| Ingredient | mg/ml | mg/ml |
|---|---|---|
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70° C.
2. Cool to 25.35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22 membrane and fill into appropriate containers.
6. Terminally sterilize the units by autoclaving.

EXAMPLE 9

Injectable Powder: (per vial)

|  | g/vial |
|---|---|
| Active Ingredient | 1.0 |
| Sodium Citrate | 1.05 | pH is adjusted to 6.2 using 0.1N citric acid solution.

Add sterile water for injection or bacteriostatic water for injection for reconstitution.

We claim:

1. (5R,6S,8R)-6-(1-hydroxyethyl)-2-(3R-pyrrolidin-2-one-3-yl)thiopenem-3-carboxylic acid, the pharmaceutically acceptable salts and pharmaceutically acceptable esters thereof.

2. A compound of claim 1 wherein the pharmaceutically acceptable salt is an alkali metal salt.

3. A compound of claim 2 wherein the alkali metal is sodium.

4. A compound of claim 1 wherein the pharmaceutically acceptable salt is an alkaline earth metal salt.

5. A compound of claim 1 wherein the pharmaceutically acceptable salt is an amine salt.

6. A compound of claim 1 wherein the pharmaceutically acceptable esters are metabolizable esters.

7. An antibacterially effective pharmaceutical composition comprising an antibacterial effective amount of a compound of claim 1 in admixture with a pharmaceutically acceptable carrier therefor.

8. A composition according to claim 7 adapted for oral administration.

9. A composition according to claim 7 adapted for parenteral administration.

10. A composition according to claim 7 adapted for topical administration.

11. A method of treating or preventing susceptible bacterial infections which comprises administering to a host in need of such treatment or prevention a compound of claim 1 or a pharmaceutical composition thereof in an amount sufficient to treat or prevent such infection.

12. A method according to claim 11 wherein the route of administration is oral.

13. A method according to claim 11 wherein the route of administration is parenteral.

14. A method according to claim 11 wherein the route of administration is topical.

* * * * *